United States Patent [19]

Atchley et al.

[11] Patent Number: 4,759,215
[45] Date of Patent: Jul. 26, 1988

[54] HIGH STRAIN CAPABILITY BALLISTIC TEST DEVICE FOR SOLID PROPELLANT ROCKET MOTORS

[75] Inventors: Rexford D. Atchley; Samuel Zeman; Tomio Sato, all of Huntsville, Ala.

[73] Assignee: Morton Thiokol, Inc., Chicago, Ill.

[21] Appl. No.: 853,588

[22] Filed: Apr. 18, 1986

[51] Int. Cl.$^4$ .............................................. G01N 3/00
[52] U.S. Cl. .................................... 73/167; 73/760; 73/788; 73/781; 374/49; 374/51
[58] Field of Search ................. 73/167, 760, 788, 818, 73/826, 766, 781, 432 SD; 374/49, 51; 33/DIG. 19

[56] References Cited

U.S. PATENT DOCUMENTS

| | | | |
|---|---|---|---|
| 3,092,992 | 6/1963 | Doner | 73/167 |
| 3,580,049 | 5/1971 | Cardwell | 73/167 |
| 4,356,720 | 11/1982 | Betts | 73/167 |
| 4,379,405 | 4/1983 | Engeler | 73/167 |
| 4,523,475 | 6/1985 | Bills | 73/781 |
| 4,569,287 | 2/1986 | Pakulak | 73/167 |

Primary Examiner—Donald P. Walsh
Attorney, Agent, or Firm—Gerald K. White

[57] ABSTRACT

A ballistic test device for simulating propellant and/or bond and/or strain conditions in a high pressure, high strain rate rocket motor. The device uses internal compliant sleeves which allow radial expansion or growth of propellants, liners and insulation or any combination of all three.

16 Claims, 5 Drawing Sheets

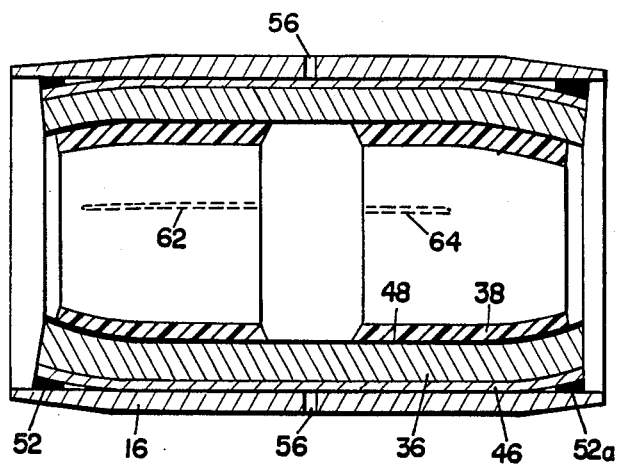
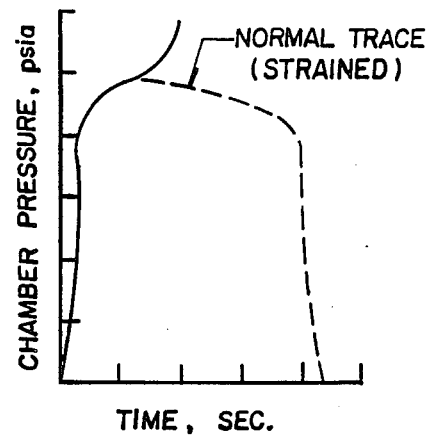
Fig. 7
Fig. 8
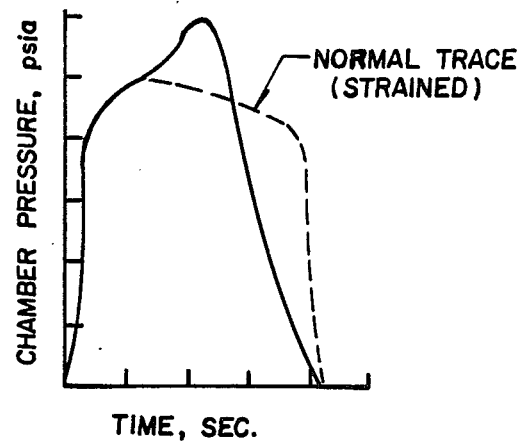
Fig. 9
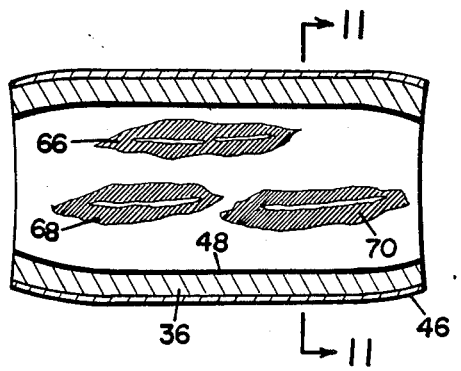
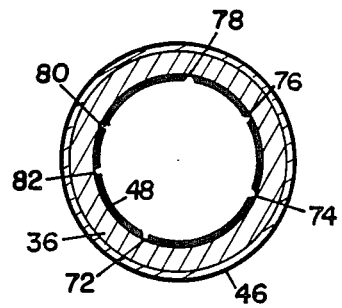
Fig. 10
Fig. 11

HIGH STRAIN CAPABILITY BALLISTIC TEST DEVICE FOR SOLID PROPELLANT ROCKET MOTORS

BACKGROUND OF THE INVENTION

1. Field of the Invention

The present invention relates to an improvement in ballistic test devices.

2. Description of the Prior Art

A ballistic test device known as the "standard ballistic test motor" has long been used in the prior art. The standard ballistic test motor, which is illustrated in FIG. 1 of the drawings herein, has been employed to evaluate certain solid rocket motor propellant characteristics, specifically the burn rate of the propellant and the effect of pressure and temperature on the burn rate.

In addition to the evaluation of these characteristics of solid rocket motor propellants, there is a need and a demand, also, for a determination and evaluation of other solid propellant characteristics that affect the operation particularly of high pressure, high strain rate rocket motors. Such other solid propellant characteristics include strain effects in the propellant bore, either burning rate enhancement or propellant strain capability, or bondline strain capability. The present invention was devised to fill the technological gap that has existed in the art in this respect.

SUMMARY OF THE INVENTION

An object of the invention is to provide an improved ballistic test device that is useful in the determination of strain effects in the propellant bore of a solid rocket motor, either burning rate enhancement or propellant strain capability, or in the evaluation of bondline strain capability.

Another object of the invention is to provide an improved ballistic test device that is useful for simulating propellant and/or bond stress and/or strain conditions in a high pressure, high strain rate rocket motor.

In accomplishing these and other objectives of the invention, the ballistic test device according to the invention uses an internal compliant sleeve which allows radial growth or expansion of propellant, liner and insulation or any combination of all three. The compliant sleeve regulates the maximum induced strain in the propellant and the location at which the maximum strain is induced.

The various features of novelty which characterize the invention are pointed out with particularity in the claims annexed to and forming a part of this specification. For a better understanding of the invention, its operating advantages and specific objects attained by its use, reference is made to the accompanying drawings and descriptive matter in which a preferred embodiment of the invention is illustrated.

BRIEF DESCRIPTION OF THE DRAWINGS

With this description of the invention, a detailed description follows with reference being made to the accompanying drawings which form part of the specification, of which:

FIG. 7 is a cross sectional view showing the test device profile when cracks are exposed;

FIG. 8 is a graph showing the chamber pressure-time history when cracks are exposed in the test device profile;

FIG. 9 is a graph showing the chamber pressure-time history of an anomalous motor compared to a normal motor;

FIG. 10 is a cross sectional view of the compliant sleeve only of the test device profile after firing and illustrates strain induced effects that are discernible upon visual inspection;

FIG. 11 is a sectional view taken along the lines 11—11 of FIG. 10;

DESCRIPTION OF THE PREFERRED EMBODIMENT

Figure 1:
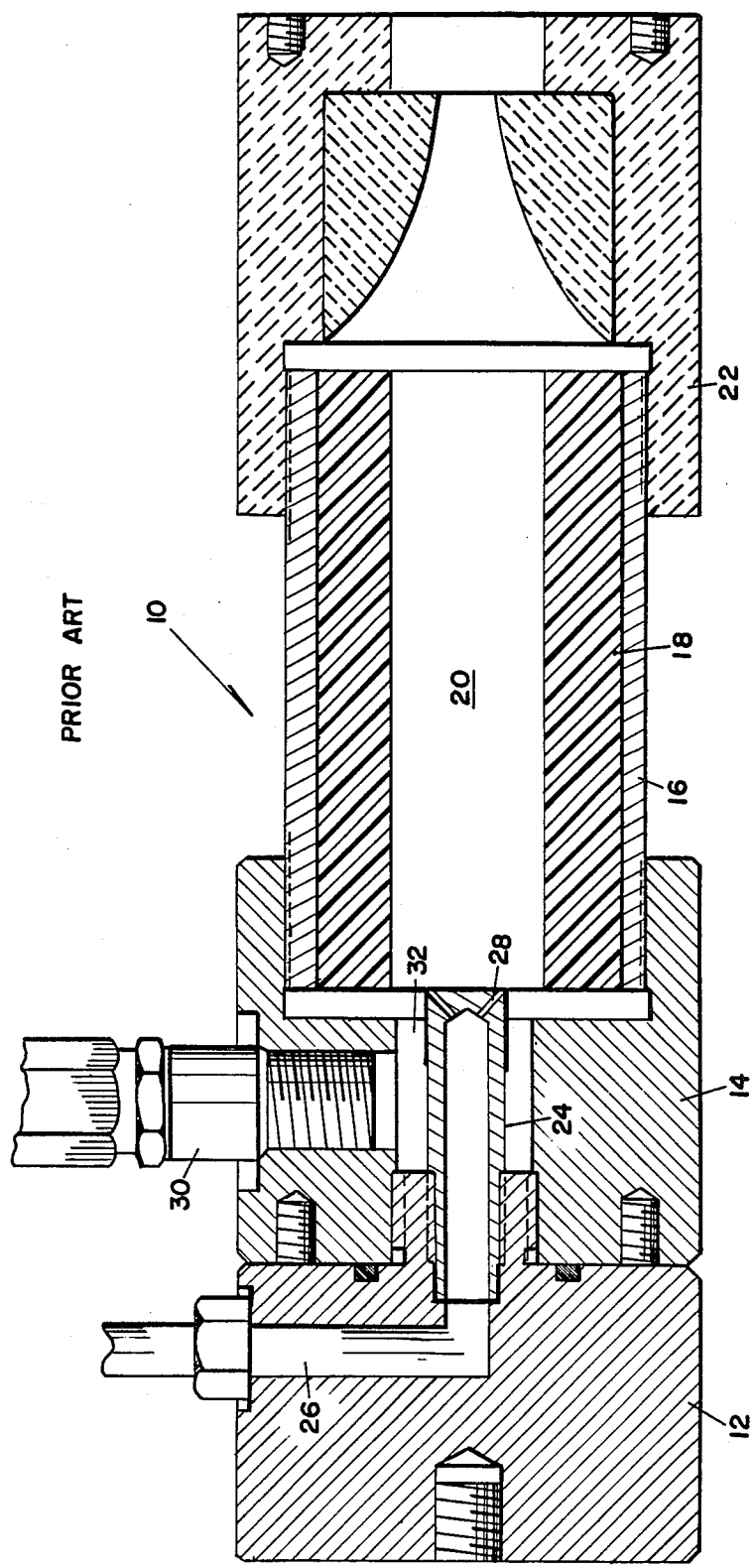
FIG. 1 is a cross sectional view illustrating the prior art standard ballistic test motor.

Referring to the drawings, the reference numeral 10 in FIG. 1 designates a typical standard ballistic test motor as known in the prior art. The motor 10 includes an igniter 12, a head closure cap 14, a cylindrical case 16, a cylindrical elongated propellant 18 having a longitudinally extending bore or chamber 20 therein, and a nozzle 22. While omitted from the drawing for purposes of simplification of the drawing, the igniter 12 includes a pyrotechnic that is contained in a tubular igniting member 24. The pyrotechnic includes a suitable squib that is connected by electrical conductors (not shown), in a conduit 26, to a suitable electrical energizing source (not shown). Hot flaming gases produced by the pyrotechnic, when activated, issue from ports 28 in the end of igniting member 24 and are caused to impinge on the walls of chamber 20, thereby effecting ignition of propellant 18. To that end, the tubular igniting member 24 extends through the head cap 14 into cooperative relationship with the walls of chamber 20. The igniter 12, as shown, is fixedly attached to the head or forward end of the head cap 14.

Also fixedly attached to the head cap 14, at a sidewall portion thereof, is a conduit 30, which conduit 30 in cooperation with an annular opening 32 in head cap 14, provides a communicating path between the chamber 20 and a suitable external pressure measuring means (not shown).

The case 16 of the standard ballistic test motor 10 may comprise a rigid heavy walled cylindrical tube that is four inches long and has an internal diameter of two inches.

In the use thereof, the standard ballistic test motor 10 typically is placed in a temperature conditioning chamber for a period of time that is sufficiently long to bring the propellant 18 to a stable temperature, for example, −65° F. The propellant 18 is then ignited by activation of the contained pyrotechnic and the relationship of the pressure in chamber 20 with respect to time is plotted as the web of propellant 18 burns through. Such pressure-time trace information may be obtained for a number of different similarly conditioned propellant temperatures at ignition to enable a determination of the average time to burn through the propellant web to be made, and an evaluation to be made, also, of the effect of pressure and temperature on the burn rate of the propellant.

Figure 2:
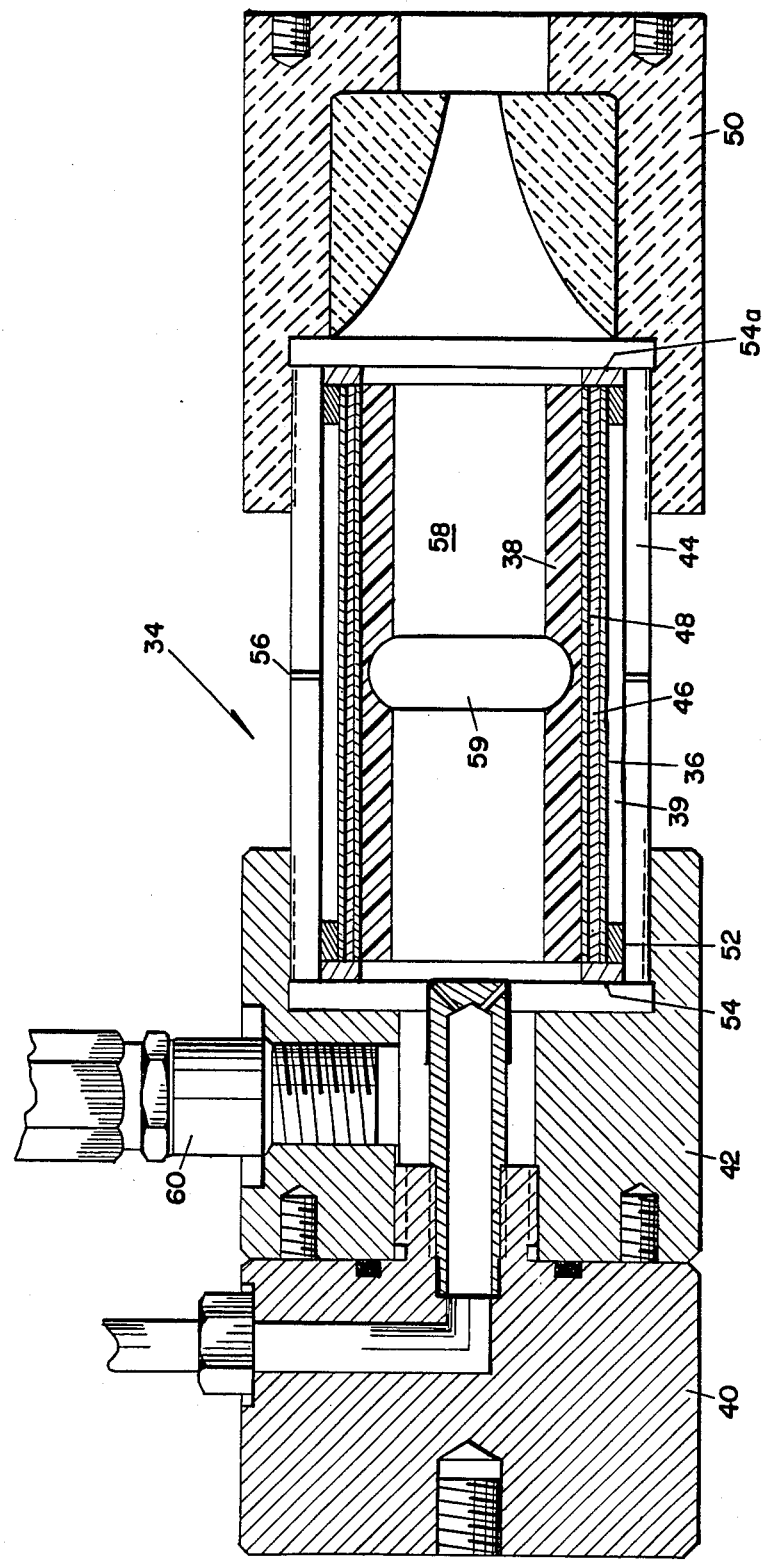
FIG. 2 is a cross sectional view of the ballistic test device according to the invention.

The ballistic test device according to the present invention, designated by the reference numeral 34 in FIG. 2, is similar in construction in certain respects to the prior art standard ballistic test motor 10, but differs significantly therefrom by the inclusion in the structure of a compliant sleeve 36. The compliant sleeve 36 surrounds an elongated cylindrical propellant 38 and enables the regulation in the propellant 38 of maximum induced strain and the location therein at which the maximum strain is induced.

As shown in FIG. 2, the ballistic test device 34 includes, in addition to the compliant sleeve 36 and propellant 38, an igniter 40, a head closure cap 42, a cylindrical case 44, insulation 46, a cylindrical liner 48, a nozzle 50, cylindrical spacers 52 and 52a and inhibitors 54 and 54a. Spacers 52 and 52a, which are ring-shaped, are positioned around the ends of compliant sleeve 36 and provide an annular space 39 between the compliant sleeve 36 and the surrounding inner wall of case 44 for that portion of sleeve 36 between the spacers 52 and 52a.

The case 44 may be a rigid heavy walled tube that is four inches long with a two inch internal diameter. Four small holes 56 that are spaced 90° apart around the periphery of the case 44 act as vents for the annular space 39 between the compliant sleeve 36 and the inner wall of the case 44.

The igniter 40, head cap 42 and nozzle 50 of the ballistic test device 34 may be identical to the igniter 12, head cap 14 and nozzle 22 of the standard ballistic test motor 10. Igniter 40, head cap 42 and nozzle 50 thus may comprise standard ballistic test motor components.

Propellant 38 of test device 34, similarly to the propellant 18 of test motor 10 has a symmetrically positioned longitudinal bore or chamber therein. The chamber in propellant 38, designated by reference numeral 58, is seen in FIG. 2, however, to include a radial groove 59 at the center of the propellant 38. For some tests, as explained hereinafter, the radial groove 59 is omitted. The pressure in chamber 58, similarly to that in chamber 20 of propellant 18, is measured by suitable means (not shown) through a conduit 60 attached to the head-end closure head cap 42 of the test device 34.

The ballistic test device 34 may be used to determine strain effects in the propellant bore or chamber 58, either burning rate enhancement or propellant strain capability, or it may be used to evaluate bondline strain capability.

When being used to evaluate internal bore conditions, compliant sleeve 36 is made of an elastomeric material. For such evaluation, no radial groove 59 would be provided in the propellant 38 at the center thereof.

Figure 15:
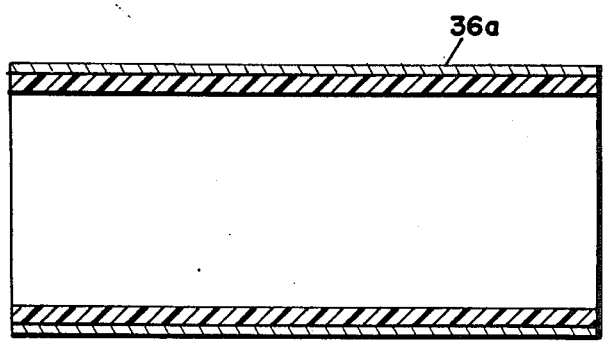
FIG. 15 is a cross sectional illustration of a modified form of compliant sleeve made of low strength metal with elastomeric build-up.

In order to evaluate bondline conditions, the compliant sleeve 36a may be made of a low strength metal, for example, with internal elastomeric build-up, as illustrated in FIG. 15 by sleeve 36a. The low strength metal sleeve 36 serves to simulate the stress state at the bondline in rocket motor applications. The radial groove 59 in the propellant serves as a stress relief mechanism for strains in the bore or chamber 58 as well as a failure detection probe.

Both elastomeric thickness and free radial displacement of the compliant sleeve 36 or 36a are used to tailor the test specimens to achieve various magnitudes at the critical interface. Free displacement of the sleeve 36 is determined by the difference in radius of the sleeve and the bore of the surrounding thick-walled case 44.

Figure 3:
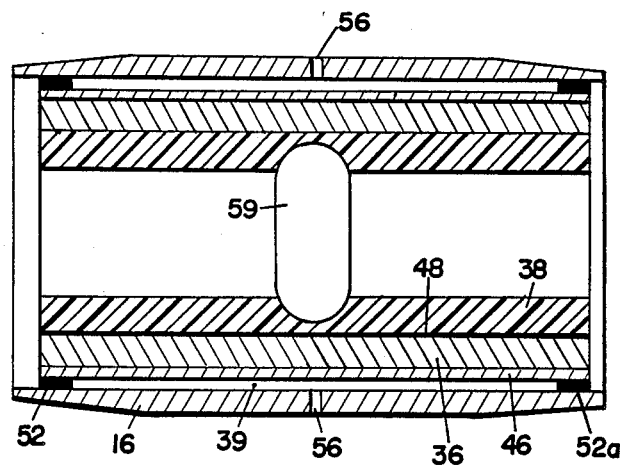
FIG. 3 is a cross sectional view of the propellant grain and support structure therefor, before ignition, of the ballistic test device of FIG. 2, which propellant grain and support structure, for convenience, are referred to hereinafter as the "test device profile"
Figure 4:
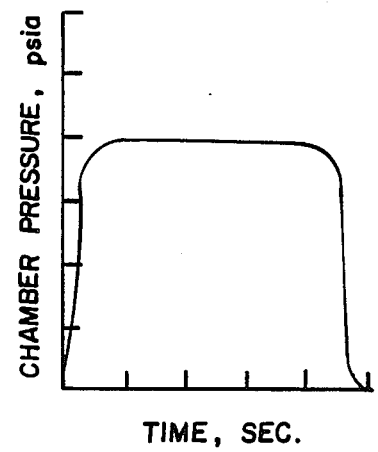
FIG. 4 is a graph showing a normal unrestrained chamber pressure-time trace of the test device profile of FIG. 3.

Prior to ignition and pressurization, the test device profile comprising the propellant grain 38 and support structure therefor including case 44, compliant sleeve 36, insulation 46, liner 48 and spacer 52, is as shown in FIG. 3.

Figure 5:
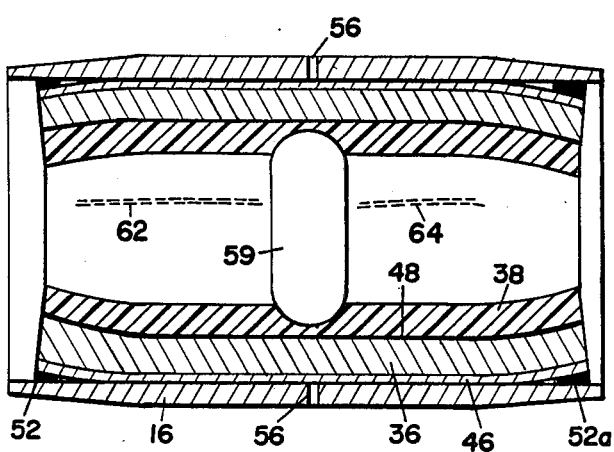
FIG. 5 is a cross sectional view of the test device profile at ignition.

As the test device profile pressurizes, the compliant sleeve 36 supporting the propellant 38 is expanded outwardly toward the inner wall of the case 44, as shown in FIG. 5, thus inducing a known strain (gradient) in the propellant 38, liner 48 and insulation 46. If the induced strain, occurring under dynamic conditions, is greater than the material capability, a crack will develop. The induced strain is highest at the inner bore of the propellant, but cracks may or may not occur in the zone depending upon the specific strain capability of the bulk propellant 38.

Figure 6:
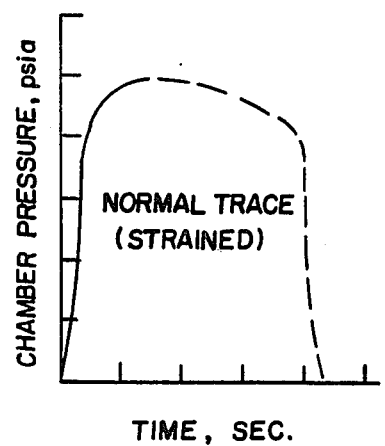
FIG. 6 is a graph showing the chamber pressure-time history, at ignition, of the test device profile.

On the other hand, cracks may occur in the liner or in that portion of the propellant 38 located in contact with (or near) the liner 48 (at the bond line) due to weak or degraded properties in proportion to the induced strains. If cracks occur along the bond line, as indicated by the reference numerals 62 and 64 in FIG. 5, and do not propagate extensively, the pressure-time history may be normal, as shown by the solid trace in FIG. 6. Post-firing visual examination of the compliant sleeve 36 is a method that may be used to detect this anomaly.

As the burning surface regresses, as shown in FIG. 7, the flame front advances to the crack(s) 62 and 64. The chamber pressure-time history obtained when cracks are exposed is illustrated by the solid trace in FIG. 8, from which trace an increase in burning surface may be noted.

The overall chamber pressure-time history produced by the test device 34 is noticeably abnormal if bondline cracks occur. This is illustrated by the solid trace in the graph of FIG. 9.

If no cracks occur during pressurization, then the chamber pressure-time traces will be more as represented by the dash lines in the graphs of FIGS. 4, 6, 8 and 9.

The ballistic test device 34 of the present invention also offers a means of easy visual confirmation of strain induced effects, even if these effects are not noticeable in the chamber pressure-time history graphs plotted during the tests. The compliant sleeve 36 is easily removable from the ballistic device 34 and may be radiographically inspected without the added thickness of the test chamber wall of case 44, or it may be sectioned longitudinally, as illustrated in FIG. 10, or radially, as illustrated in FIG. 11.

As seen in FIG. 10, cracks in the propellant 38 will result in easily identifiable char areas 66, 68 and 70 on the liner 48. Also, if cracks occur in the liner 48, around the periphery thereof, these are easily identifiable, as seen in FIG. 11, being indicated by reference numerals 72, 74, 76, 78, 80 and 82.

Figure 12:
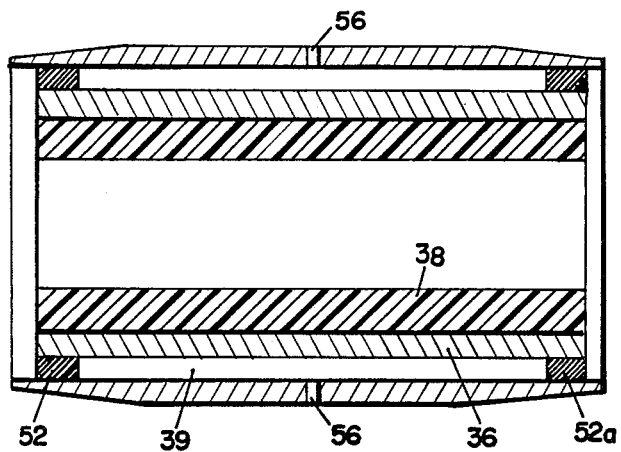
FIG. 12 is a cross sectional view of a modification of the test device profile of FIG. 3, before ignition, for producing high bore strains.
Figure 13:
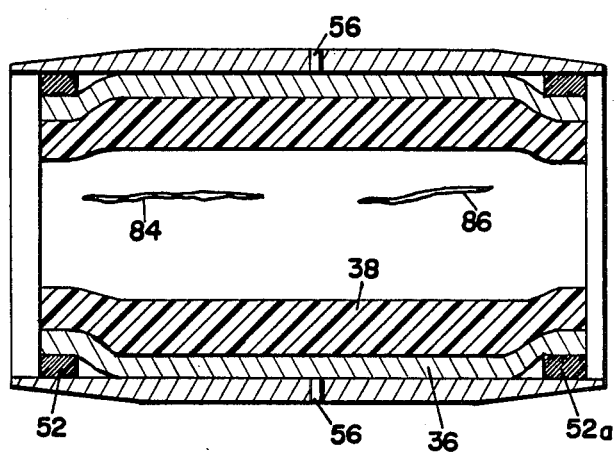
FIG. 13 is a cross sectional view showing the FIG. 12 test device profile modification after ignition.
Figure 14:
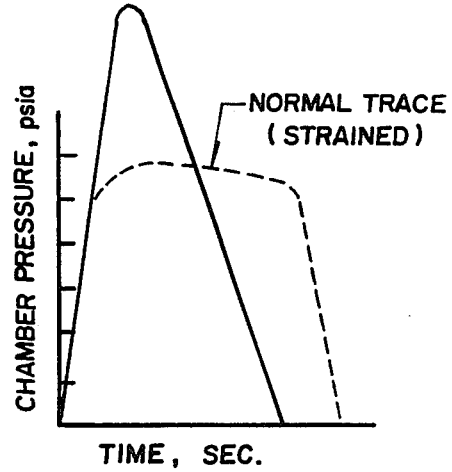
FIG. 14 is a graph showing the abnormal trace produced by surface cracks in the propellant in the modified test device profile of FIG. 13.

The ballistic test device 34 can also be designed to produce high bore strains, as shown by the test device profile of FIG. 12. If surface cracks occur on ignition, as indicated by reference numerals 84 and 86 in FIG. 13, a distinctive abnormal chamber pressure-time history will result, as shown by the solid trace of graph of FIG. 14.

Thus, in accordance with the invention, there has been disclosed a ballistic test device for solid propellant rocket motors that has utility in the evaluation of strain effects in the propellant bore, either burning rate enhancement or propellant strain capability, or in the evaluation of bondline strain capability. The disclosed ballistic test device is operative to simulate propellant and/or bond stress and/or strain conditions in a high pressure, high strain rate rocket motor. The device uses internal compliant sleeves which allow radial expansion or growth of propellants, liners and insulation.

With this description of the invention in detail, those skilled in the art will appreciate that modifications may be made to the invention without departing from its spirit. Therefore, it is not intended that the scope of the invention be limited to the specific embodiments illustrated and described. Rather, it is intended that the scope of the invention be determined by the appended claims and their equivalents.

What is claimed is:

1. A ballistic test device for evaluating solid rocket motor propellant characteristics comprising,
    a solid propellant to be evaluated, said propellant being cylindrical in form and having a symmetrically positioned cylindrical bore therein forming a chamber,
    a nozzle communicating with one end of said chamber,
    a closure cap for the other end of said chamber,
    conduit means in said closure cap through which the pressure in said chamber may be measured, and
    structural support means for said propellant comprising a compliant sleeve positioned in closely surrounding relation to said propellant and an outer rigid cylindrical case in which said propellant and compliant sleeve are symmetrically positioned and including spacer means positioned at the ends of said compliant sleeve spacing said compliant sleeve from said case thereby to form an annular space into which said compliant sleeve may move for allowing radial expansion of said propellant upon ignition thereof.

2. A ballistic test device as specified in claim 1 wherein a centrally positioned radial groove is provided in the bore of said propellant.

3. A ballistic test device as specified in claim 1 wherein a cylindrical liner and cylindrical insulation are positioned between said propellant and said compliant sleeve with said liner adjoining said propellant.

4. A ballistic test device as specified in claim 3 further including an inhibitor ring adjacent each end of said propellant.

5. A ballistic test device as specified in claim 4 wherein a centrally positioned radial groove is provided in the bore of said propellant.

6. A ballistic test device as specified in claim 1 wherein said compliant sleeve is made of low strength metal with internal elastomeric build-up.

7. A ballistic test device for simulating propellant and/or bond stress and/or strain conditions in a high pressure, high strain rate rocket motor comprising,
    a solid propellant to be evaluated, said propellant being cylindrical in form and having a symmetrically positioned cylindrical bore therein forming a chamber,
    a nozzle communicating with one end of said chamber,
    a closure cap for the other end of said chamber,
    conduit means in said closure cap through which the pressure in said chamber may be measured, and
    structural support means for said propellant comprising a compliant sleeve positioned in closely surrounding relation to said propellant, with a liner and insulation therebetween, and an outer rigid cylindrical case in which said propellant and compliant sleeve are symmetrically positioned with an inhibitor ring at each end of said compliant sleeve and including spacer means positioned at each of the ends of said compliant sleeve spacing said compliant sleeve from said case thereby to form an annular space into which said compliant sleeve may move for allowing radial expansion of said propellant upon ignition thereof.

8. A ballistic test device as specified in claim 7 wherein a centrally positioned radial groove is provided in the bore of said propellant.

9. A ballistic test device as specified in claim 7 wherein said compliant sleeve is made of low strength metal with internal elastomeric build-up.

10. A test device structure comprising
    a propellant to be evaluated, said propellant being cylindrical in form and having a symmetrically positioned bore therein, and
    structural support means for said propellant comprising a compliant sleeve positioned in closely surrounding relation to said propellant and an outer rigid cylindrical case in which said propellant and compliant sleeve are symmetrically positioned and including spacer means positioned at the ends of said compliant sleeve and case and spacing said compliant sleeve from said case thereby to form an annular space into which said compliant sleeve may move upon radial expansion of said propellant and compliant sleeve.

11. A test device structure as specified in claim 10 wherein said case comprises a rigid heavy wall tube.

12. A test device structure as specified in claim 10 further including holes in the wall of said case for venting the space between said compliant sleeve and the inner wall of said case upon radial expansion of said compliant sleeve and propellant.

13. A test device structure as specified in claim 10 wherein a centrally positioned groove is provided in the bore of said propellant.

14. A test device structure as specified in claim 10 wherein a cylindrical liner and cylindrical insulation are positioned between said propellant and said compliant sleeve with said liner adjoining said propellant.

15. A test device structure as specified in claim 10 wherein said compliant sleeve is made of low strength metal with internal elastomeric build-up.

16. A test device structure as specified in claim 1 wherein said case comprises a rigid heavy wall tube having holes in the wall thereof for venting the space between said compliant sleeve and the inner wall of said case upon radial expansion of said compliant sleeve and propellant,
    wherein a centrally positioned groove is provided in the bore of said propellant, and
    wherein a cylindrical liner and cylindrical insulation are positioned between said propellant and said compliant sleeve with said liner adjoining said propellant.

* * * * *